US008219413B2

(12) United States Patent
Martinez et al.

(10) Patent No.: US 8,219,413 B2
(45) Date of Patent: Jul. 10, 2012

(54) IDENTIFICATION SYSTEM AND METHOD FOR MEDICATION MANAGEMENT

(75) Inventors: John D. Martinez, San Diego, CA (US); James P. Wilkinson, San Diego, CA (US); Thomas C. Steinhauer, San Diego, CA (US); Kimberly Frazier, Laguna Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 1446 days.

(21) Appl. No.: 11/351,854

(22) Filed: Feb. 11, 2006

(65) Prior Publication Data
US 2006/0229551 A1    Oct. 12, 2006

Related U.S. Application Data

(60) Provisional application No. 60/652,134, filed on Feb. 11, 2005.

(51) Int. Cl.
*G06Q 50/00* (2012.01)
(52) U.S. Cl. .......................................................... 705/2
(58) Field of Classification Search .................. 705/2, 3, 705/4
See application file for complete search history.

(56) References Cited

U.S. PATENT DOCUMENTS

| | | | |
|---|---|---|---|
| 4,853,521 | A | 8/1989 | Claeys et al. |
| 5,681,285 | A | 10/1997 | Ford et al. |
| 5,713,856 | A | 2/1998 | Eggers et al. |
| 5,941,846 | A | 8/1999 | Duffy et al. |
| 5,957,885 | A | 9/1999 | Bollish et al. |
| 6,415,978 | B1 | 7/2002 | McAllister |
| 2002/0169636 | A1* | 11/2002 | Eggers et al. ............ 705/3 |

(Continued)

FOREIGN PATENT DOCUMENTS
JP    11-502132    2/1992
(Continued)

OTHER PUBLICATIONS

Medly System with Bar Code Module, Alaris Medical Systems, Inc., Premarket Notification 510(k) No: K04124, U.S. Food and Drug administration (FDA), Jul. 7, 2004, XP007908778.

(Continued)

*Primary Examiner* — Gerald J. O'Connor
*Assistant Examiner* — John Pauls
(74) *Attorney, Agent, or Firm* — McDermott Will & Emery LLP (57) ABSTRACT

An identification system and method for medication management comprises a controller, a drug library accessible by the controller, the drug library containing drug library profiles including a data set of drug information, and an identification module configured to read patient identification information from machine-readable identification devices worn by patients and to read drug information from machine-readable identification devices affixed to drugs or containers of drugs. The controller compares the read information to each other and to the drug library profile and provides alerts or error signals in the event of an inconsistency. In one case, identification devices are read by an optical reader fixedly mounted to the identification module. In another case, identification devices are read by an optical reader that is hand-held and mobile and can be moved to the location of the identification device. The hand-held reader communicates with the identification module by wired or wireless means. In another case, a third reader that is non-optical and wireless is fixedly mounted to the identification module. The controller is also configured to provide alerts or error messages in the event that there is an inconsistency between the drug information on the drug or drug container when compared to the drug library profile associated with the controller.

36 Claims, 5 Drawing Sheets

U.S. PATENT DOCUMENTS

| | | |
|---|---|---|
| 2003/0074223 A1 | 4/2003 | Hickle et al. |
| 2003/0106553 A1 | 6/2003 | Vanderveen |
| 2003/0135388 A1 | 7/2003 | Martucci et al. |
| 2003/0139701 A1 | 7/2003 | White et al. |
| 2004/0051368 A1 | 3/2004 | Caputo et al. |
| 2004/0128162 A1* | 7/2004 | Schlotterbeck et al. .......... 705/2 |
| 2004/0193453 A1* | 9/2004 | Butterfield et al. ............... 705/2 |
| 2005/0108057 A1 | 5/2005 | Cohen et al. |
| 2005/0144043 A1 | 6/2005 | Holland et al. |
| 2006/0047538 A1* | 3/2006 | Condurso et al. ................. 705/3 |

FOREIGN PATENT DOCUMENTS

| | | |
|---|---|---|
| WO | WO 03/053503 | 7/2003 |
| WO | WO 03/063932 | 8/2003 |

OTHER PUBLICATIONS

EPO Communication dated Jul. 16, 2009, from related application EP08007827.2.

International Search Report, PCT/US2006/004940, Feb. 11, 2006, Cardinal Health 303, Inc.

Examination Report from EP08007827.2-2201, mailed Nov. 24, 2008.

European Search Report dated Apr. 8, 2011 for EP10 01 1596 in 11 pages.

Japanese Office Action for JP Pat. App. No. 2007-55300 dated Jun. 14, 2011.

* cited by examiner

IDENTIFICATION SYSTEM AND METHOD FOR MEDICATION MANAGEMENT

CROSS-REFERENCES TO RELATED APPLICATIONS

This application claims the benefit of U.S. Provisional Application No. 60/652,134, filed on Feb. 11, 2005.

BACKGROUND OF THE INVENTION

The present invention relates generally to fluid infusion and more particularly, to identifying a patient and medication so that correct medication is infused into a patient.

Physicians and other medical personnel apply intravenous ("IV") infusion therapy to treat various medical complications in patients. IV infusion therapy typically involves infusing medical fluids, such as drugs or nutrients, from a fluid supply, such as a bag, bottle, or other container, through the tube of a fluid administration set to a cannula inserted into a patient's blood vessel. In a typical facility, a physician enters an order for medication for a particular patient. This order may be handled either as a simple prescription slip, or it may be entered into an automated system, such as a physician order entry ("POE") system. The prescription slip or the electronic prescription from the POE system is routed to the pharmacy, where the order is checked, then filled. Typically, pharmacies check the physician order against possible allergies of the patient and for possible medication interactions in the case where two or more medications are prescribed, and also check for contra-indications. For a medication that is to be delivered by IV, the prescribed medication is prepared by a pharmacist and added to a bag or bottle or other suitable container at the pharmacy. A pharmacist also typically identifies the prepared order, identifies the contents of the bag or bottle, and identifies the patient for whom the bag or bottle is intended with a paper label that is attached to the bag or bottle and in some cases by other means, such as, for example, including a bar code or magnetic device, or by use of a radio frequency (RF) signal interactive device such as an RFID tag. In the case of non-IV drugs, such as oral medications, the drug may itself be labeled with the order or drug information (including the patient identifier) or may be inserted into a container that is labeled. Depending on the facility, the medication may be placed into a transport carrier for transport to a nurse station. Once at the nurse station, the prescriptions are once again checked against the medications that have been identified for delivery to ensure that no errors have occurred. If all is in order, the medication is subsequently administered to the patient.

Medication errors, that is, errors that occur in the ordering, dispensing, and administration of medications, regardless of whether those errors caused injury or not, are a significant consideration in the delivery of healthcare in the institutional setting. Additionally, adverse drug events ("ADE"), defined as injuries involving a drug that require medical intervention and representing some of the most serious medication errors, are responsible for a number of patient injuries and death. Healthcare facilities continually search for ways to reduce the occurrence of medication errors. Various systems and methods are being developed at present to reduce the frequency of occurrence and severity of preventable adverse drug events ("PADE") and other drug errors. In the administration of drugs, focus is typically directed to the following five "rights" or factors; that is, the right drug is directed to the right patient, in the right amount, through the right route, and at the right time. Systems and methods seeking to reduce ADE's and PADE's should take these five rights into consideration.

For safety reasons and in order to achieve optimal results, the medication is often administered in accurate amounts as prescribed by the doctor and in a controlled fashion by using an infusion pump. Infusion pumps operate by displacing the fluid in a fluid administration set to force fluid from the fluid supply through the tube and into the patient. The infusion pump is programmed by a clinician, such as a nurse, with operating parameters to achieve the administration of the medication as prescribed by the physician. Such operating, or pumping, parameters are medication- and patient-specific. That is, the pumping parameters are selected based on the particular medication prescribed and the specific patient for whom they are intended. It is the nurse's responsibility to match the prescribed medication with the correct patient and with the properly programmed pump.

Medical infusion pumps have advanced greatly over the years and permit more precise infusion control resulting in much better treatment for patients. Doctors are more assured that the doses and infusion rates that they prescribe for their patients can be delivered to the patients accurately by infusion pumps to achieve optimum therapeutic effect. However, there remains a continuing concern that the right medication is matched to the right pump and to the right patient.

Prior attempts have been made to assure that the right medication is administered to the right patient through the right pump. In one example, a bar code label identifying the medication and patient is applied to the bag containing the medication at the pharmacy. After a clinician manually programs the pump, a bar code scanner connected to the pump is used to read the bar code label on the bag of medication to verify that it identifies the same medication as that programmed into the pump. In another example, a bar code label applied to the bag of medication is read with a bar code scanner built into the housing of the pump to automatically program the pump, thus avoiding manual programming entirely. However, prior art systems do not link a scanned medication or drug to a drug library entry and therefore do not give the combined protection of dose limits and right drug, right patient. However, the Medley medication safety system from ALARIS Products of Cardinal Health, San Diego, Calif., U.S.A., provides this level of protection in networked and non-networked environments.

These advanced infusion pumps have revolutionized the way intravenous ("IV") medications are delivered by providing dose limit protection, thus ensuring that the right dose of the medication is delivered to the patient. Still missing from these pumps is the ability to automatically select the right medication from the pump's drug library, ensure that the medication being administered is for the patient that is currently connected to the pump, and that the clinician administering the medication is authorized to do so.

As the name implies, multi-channel infusion pumps have more than one pumping channel, and a respective infusion line or administration set can be installed into each channel. This arrangement allows the pump of each channel to be programmed to deliver the particular medication that flows through the respective infusion line or set installed in the channel such that each line may deliver a different medication at different rates or in different volumes. In cases where a single patient may be prescribed multiple simultaneous infusions for different medications, sometimes four or more, the multi-channel infusion pump provides a distinct advantage. Each channel of a single pump may be programmed differently. Such multi-channel infusion pumps may be modular, in which case the number of channels may be varied, or may be fixed, such as a dual-channel pump. In most cases, all channels of a multi-channel infusion pump are under the control of a common controller or processor. Alternatively, multiple single-channel pumps may be used to simultaneously infuse multiple medications into a patient. One potential problem that exists when infusing a patient with multiple infusion medications, whether through a multi-channel pump or through multiple single-channel pumps, is ensuring that each infusion channel or pump is properly programmed to deliver its respective medication. That is, the particular pump or channel of a pump is properly programmed to deliver the particular medication of the container to which the fluid line of that channel or pump is connected.

Moreover, even where the right medication arrives at the right patient for administration, and the correct medication in each infusion line is known, that medication may regardless be administered incorrectly in the case where the pump is programmed with incorrect infusion parameters. For example, even where the medication order includes the correct infusion parameters, those parameters may be incorrectly entered into al infusion pump causing the infusion pump to administer the medication in a manner that may not result in the prescribed treatment. The nurse may also start an infusion at the wrong time or forget to administer an infusion, resulting in incorrect treatment that may interfere with other scheduled medications prescribed by the physician. Such incorrect administration of the medication may occur even where the medication is to be administered using an automated or semi-automated administration device, such as an infusion pump, if the automated device is programmed with incorrect medication administration parameters. Even in an automated system where the medication has a bar code and that bar code includes infusion parameters, errors can occur. The bar code may have been improperly printed or may have been smudged so that it cannot be read accurately and in fact is read inaccurately. In other cases, the bar code may simply be incorrect. Because of such a risk, some health care facilities do not permit a bar code to be used for anything other than patient identification and medication identification. Such facilities prefer clinicians to manually program infusion pumps in that facility.

Even though the multi-channel and single-channel infusion pumps of today have provided significant advances in the art to avoid medication errors and have reduced the likelihood of such medication errors substantially, further improvements are possible and desired. Hence, those skilled in the art have recognized a need for an automatic identification system and method to associate the patient with the correct medication. Further, those skilled in the art have recognized a need for a more accurate system and method for programming operating or pumping parameters into infusion pumps so that errors are avoided. The present invention fulfills this need and others.

SUMMARY OF THE INVENTION

Briefly and in general terms, the present invention is directed to an identification system and method for medication management. In accordance with a system of the invention, there is provided a drug library comprising a plurality of drug library profiles, each one of the drug library profiles defining a data set of drug information, an identification module configured to obtain drug information from machine-readable information devices affixed to drugs or containers of drugs and to obtain patient information from machine-readable information devices worn by patients, and configured to communicate the drug information and patient information, and a controller in communication with the identification module, the controller configured to: access the drug library to associate a drug library profile with the controller, receive the patient information from the identification module, receive the drug information from the identification module, the drug information including patient information for whom the drug is to be administered, determine whether the patient information received from the identification module from the machine-readable information device worn by a patient is consistent with the patient information contained in the drug information received from the identification module, and determine whether the drug information received from the identification module is consistent with the drug library profile associated with the controller.

In more detailed aspects, the controller is configured to display an alert message when the patient information received from the identification module is not consistent with the patient information received from the drug or drug container. The controller is also configured to display an alert message when the drug information includes a drug identifier that is not in the data set of drug information of the drug library profile associated with the controller. Further, the controller is configured to display an alert message when the drug information includes a drug concentration that is not consistent with the data set of drug information in the drug library profile associated with the controller, and in a further aspect, the controller is configured to display an alert message when the drug information includes a drug dose that is not consistent with the data set of drug information in the drug library profile associated with the controller.

In further aspects, the system further comprises a server in communication with the controller, the server configured to provide the controller with a medication order for the selected patient. The drug library is integral with the controller. In another aspect, the drug library is accessible by the controller through a remote server, and in a further aspect, the identification module is selectively detachable from the controller.

In other detailed aspects, the identification module comprises a bar code reader for reading bar code-type information devices, the identification module comprises a RFID reader for reading RFID-type information devices, and the identification module comprises a hand-held mobile reader configured to read information devices located remotely from the identification module. In accordance with other details, the identification module further comprises a bar code reader fixed in position at the identification module for reading bar code-type information devices brought to its proximity to be read, a RFID reader fixed in position at the identification module for reading RFID-type information devices brought to its proximity to be read, and the hand-held mobile reader is connected with the identification module through a wired or wireless connection.

In another system detailed aspect, an infusion pump is connected with the controller and the controller is adapted to provide programming parameters to the infusion pump that are received from the drug or drug container information device through the identification module.

In further aspects in accordance with the invention, there is provided an identification system for medication management, for use with an infusion pump, the system comprising: an infusion pump, a drug library comprising a plurality of drug library profiles, each one of the drug library profiles defining a set of drug identifiers, drug concentrations, and drug doses, a controller configured to provide pumping parameters to the infusion pump and configured to access the drug library to associate the controller with a drug library profile, an identification module configured to obtain drug information from machine-readable identification devices affixed to drugs or containers of drugs and to obtain patient identification information from machine-readable identification devices worn by patients, and configured to communicate the drug information and patient identification information, and a communications interface processor in communication with the controller and the identification module, the interface processor configured to: receive patient identification information from the identification module, receive drug information from the identification module, the drug information including a patient identifier, a drug identifier, a drug concentration, and a drug dose, determine whether the patient identification information received from the identification module matches the patient identifier received from the drug information from the identification module, and determine whether the drug information received from the identification module is consistent with the drug library profile based at least on comparisons between the received patient identification information, the received drug information, and information from the drug library profile associated with the controller, and provide the controller with infusion pump programming parameters. In another aspect, the infusion pump is selectively detachable from the controller.

In a method in accordance with aspects of the invention, there is provided an identification method for medication management, the method comprising: reading a machine-readable identification device worn by a patient to obtain patient identification information, reading a machine-readable identification device affixed to a selected drug or drug container to obtain drug information that includes a patient identifier, a drug identifier, a drug concentration, and a drug dose, comparing the patient identification information from the identification device worn by the patient to the patient identifier from the identification device affixed to the drug or drug container, communicating a first error message when the patient identification information does not match the patient identifier, comparing the drug identifier from the identification device affixed to the drug or drug container to a set of drug identifiers of a drug library profile, communicating a second error message when the drug identifier is not within the set of identifiers of the drug library profile, comparing the drug concentration from the identification device affixed to the drug or drug container to a set of drug concentrations of the drug library profile, communicating a third error message when the read drug concentration is not within the set of concentrations of the drug library profile, comparing the read drug dose from the identification device affixed to the drug or drug container to a set of drug doses of the drug library profile, communicating a fourth error message when the read drug dose is not within the set of drug doses of the drug library profile, and providing infusion pump programming parameters, the programming parameters corresponding to the read drug dose.

In further more detailed method aspects, the method further comprises manually confirming that the infusion pump programming parameters agree with a medication order for the patient. In another aspect, either step of reading further comprises reading with a reader that is fixed in position such that information or identification devices to be read must be moved to the proximity of the bar code reader. In another aspect, either step of reading further comprises reading with a reader that is mobile and hand-held such that the hand-held reader may be brought to the proximity of information or identification devices to be read. Either step of reading further comprises reading either with a reader that is fixed in position such that information or identification devices to be read must be moved to the proximity of the bar code reader or with a reader that is mobile and hand-held such that the hand-held reader may be brought to the proximity of information or identification devices to be read, and further wherein one of the readers is optical and another is the readers is wireless but non-optical.

In other system aspects, there is provided an identification system for medication management, for use with an infusion pump and a physiological monitor, the system comprising: an infusion pump, a drug library accessible by the controller and comprising a plurality of drug library profiles, each one of the drug library profiles defining a set of drug identifiers, drug concentrations, drug doses, and a physiological level, a physiological monitor providing a physiological level, an identification module configured to obtain drug information from machine-readable identification devices affixed to drugs or containers of drugs and to obtain patient identification information from machine-readable identification devices worn by patients, and configured to communicate the drug information and patient identification information, and the controller in communication with the identification module and physiological monitor, the interface communications processor configured to: receive patient identification information from the identification module from the machine-readable identification device worn by a patient, receive drug information from the identification module from the machine-readable identification device affixed to a drug or drug container, the drug information including a patient identifier, a drug identifier, a drug concentration, and a drug dose, receive a physiological level from the physiological monitor, communicate a first error signal when the drug information includes a patient identifier that does not match the patient identification derived from the machine-readable identification device worn by the selected patient, communicate a second error signal when the drug information includes a drug identifier that is not in the set of drug identifiers of the drug library profile associated with the controller, communicate a third error signal when the drug information includes a drug concentration that is not in the set of drug concentrations of the drug library profile associated with the controller, communicate a fourth error signal when the drug information includes a drug dose that is not in the set of drug doses of the drug library profile associated with the controller, communicate a fifth error signal when the physiological level from the physiological monitor is not consistent with the physiological level in the drug library profile associated with the controller, and provide the controller with infusion pump programming parameters.

In a more detailed aspect, the physiological level in the drug library profile associated with the controller is patient specific. In another aspect, the physiological level in the drug library profile associated with the controller is drug specific. In yet a further aspect, the infusion pump programming parameters correspond to the selected drug dose.

In another aspect in accordance with the invention, there is provided an identification apparatus for medical instruments, the device comprising: a housing, a first optical reader including a first optical scanner fixed in position on the housing such that the first optical scanner faces outward from the housing with a first field of view of the first optical scanner directed outside the housing whereby an identification device must be brought to a position within the first field of view of the first scanner to be read, a second optical reader mounted within the housing with a second optical scanner that is mobile in relation to the housing having a second optical field of view whereby the second optical scanner may be carried to an identification device to place the identification device within the second optical field of view to read the identification device, a communication device for interconnecting the mobile second optical scanner with the second optical reader, and a non-optical wireless identification reader fixed in position on the housing and having a non-optical, wireless field of view directed outward from the housing whereby an identification device must be placed within the non-optical, wireless field of view to be read by the non-optical wireless identification reader.

In more detailed aspects, the non-optical reader comprises an RFID reader adapted to read RFID devices. In another aspect, the non-optical reader comprises an RFID reader adapted to read and write to RFID devices. The identification apparatus further comprises a control switch having a first position at which a reader is activated to read an identification device and a second position at which a reader at the housing is inactivated. The communication device comprises a hardwired arrangement between the mobile scanner and the housing. In another aspect, the communication device comprises a wireless communication system between the mobile scanner and the housing.

These and other features and advantages of the present invention will become apparent from the following detailed description of the preferred embodiments which, taken in conjunction with the accompanying drawings, illustrate by way of example the principles of the invention.

DETAILED DESCRIPTION OF THE PREFERRED EMBODIMENTS

Figure 1:
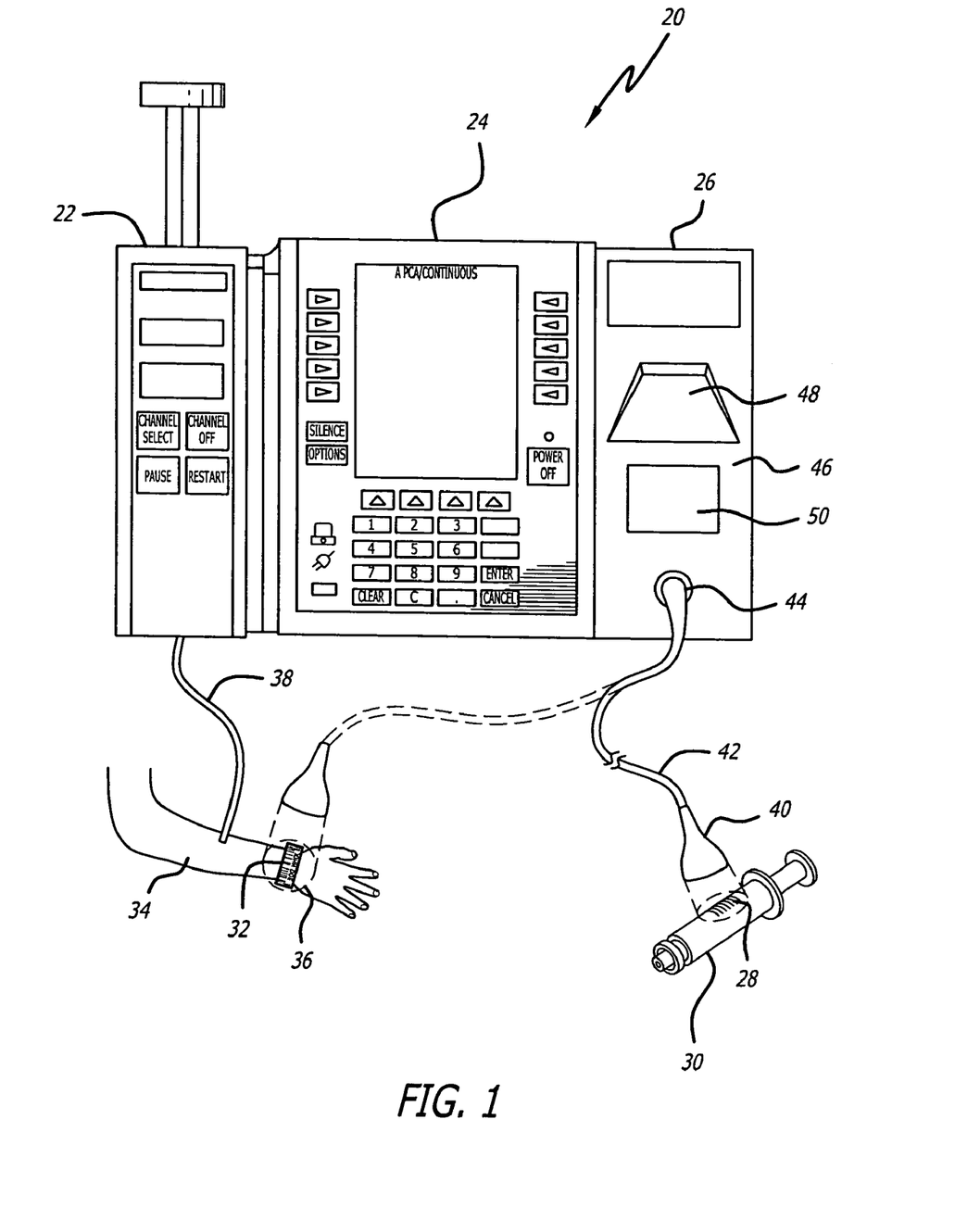
FIG. 1 is a simplified pictorial illustration of a modular infusion pump system having a syringe pump at the left side, a controller in the center, and an automatic identification module("ID module") at the right side which in this case comprises a hand-held, mobile bar code reader for reading the bar code on the syringe of medication and the bar code on the patient's wrist to identify both, a second bar code reader fixedly mounted to the housing of the ID module, and a RFID reader also fixedly mounted to the housing of the ID module.

Referring now in more detail to the drawings for purposes of illustration of embodiments of the invention wherein like reference numerals designate corresponding or like elements among the several views, there is shown in FIG. 1 a figurative view of a modular infusion pump system 20 having a syringe pump 22, a controller 24, and an automatic identification system or module ("ID module") 26. In this case the ID module includes a bar code reader for reading a bar code 28 on a syringe of medication 30 and a bar code 32 on a patient's 34 wrist band 36 to identify both.

To preserve clarity of illustration in the drawing, the syringe 30 is shown without a fluid administration set 38 that would normally be connected to its nozzle and to the patient 34; however, the connection of the administration set 38 from the syringe pump 22 (in which the syringe would be mounted for infusion of its contents) to the patient is shown in the drawing. In this case, a "tethered" or hand held bar code reader 40 is used to read the two bar codes 28 and 32. The wiring 42 of the tethered bar code reader is connected to the ID module 26 at a connector 44 on its front panel 46, although other means of connection, including wireless connections, are possible. The hand held bar code reader is mobile and is shown being brought to a remote location from the ID module to read the bar code on the syringe and as shown in dashed lines to read the bar code on the patient's identification wrist band.

In this embodiment, the ID module 26 also includes a fixed bar code reader 48 that is fixedly mounted to the front panel of the ID module. In order to read bar code information devices, such as a bar code tag, with this fixed reader, the bar code information device must be moved to the proximity of this fixed bar code reader. As with the mobile bar code reader, the fixed bar code reader comprises an optical scanner having a limited field of view. In this case, the field of view of the fixed bar code scanner is outside the ID module housing. Bar code information devices must be placed within the optical field of view of the respective scanner in order to be read by the bar code reader.

The front panel 46 of the ID module also includes an RFID antenna 50 for use with an internal RFID reader or interrogator. The reader is useful to read RFID information devices, such as RFID tags, that may be used on the syringe 30 or the patient 34 instead of, or with, the bar codes 28 and 32 respectively. Such RFID information devices may be read-only, or may be writable and may be self-powered or powered by the RFID reader, as is well known to those skilled in the art. Positioning an appropriate RFID tag proximate and within the range of the antenna on the front panel, for example within 2.5 to 8 centimeters (1 to 3 inches), allows the internal RFID reader to read the tag, and if configured so, to write to the tag as well. In this case, the RFID reader is also fixedly mounted to the ID module and information devices must be brought to it to be read. The RFID reader has a wireless, non-optical field of view directed outward from the housing of the ID module and RFID information devices must be placed within this field of view to be read.

Further details concerning a modular infusion system 20 having a central controller 24 may be found in U.S. Pat. No. 5,713,856 to Eggers et al., which is incorporated herein by reference in its entirety. The ID module 26 is connected with the controller 24. Information may flow directly between the controller and ID module. Alternatively, as will be discussed in more detail below, a communications interface board may be inserted between the controller and the ID module.

The ID module 26 contains the embedded bar code scanner 48 that can read linear, two-dimensional, and other bar code symbologies as well as the RFID reader and antenna 50 to read medication labels 28 as well as patient 34 and clinician identification devices 49. Although not shown, the clinician who operates the modular pump system 20 may also have an identification device, such as a badge, containing the identification information for the clinician that is in bar code or RFID form, or both, or other forms, that can be read by the embodiment of the ID module shown, or by a different embodiment.

Figure 2:
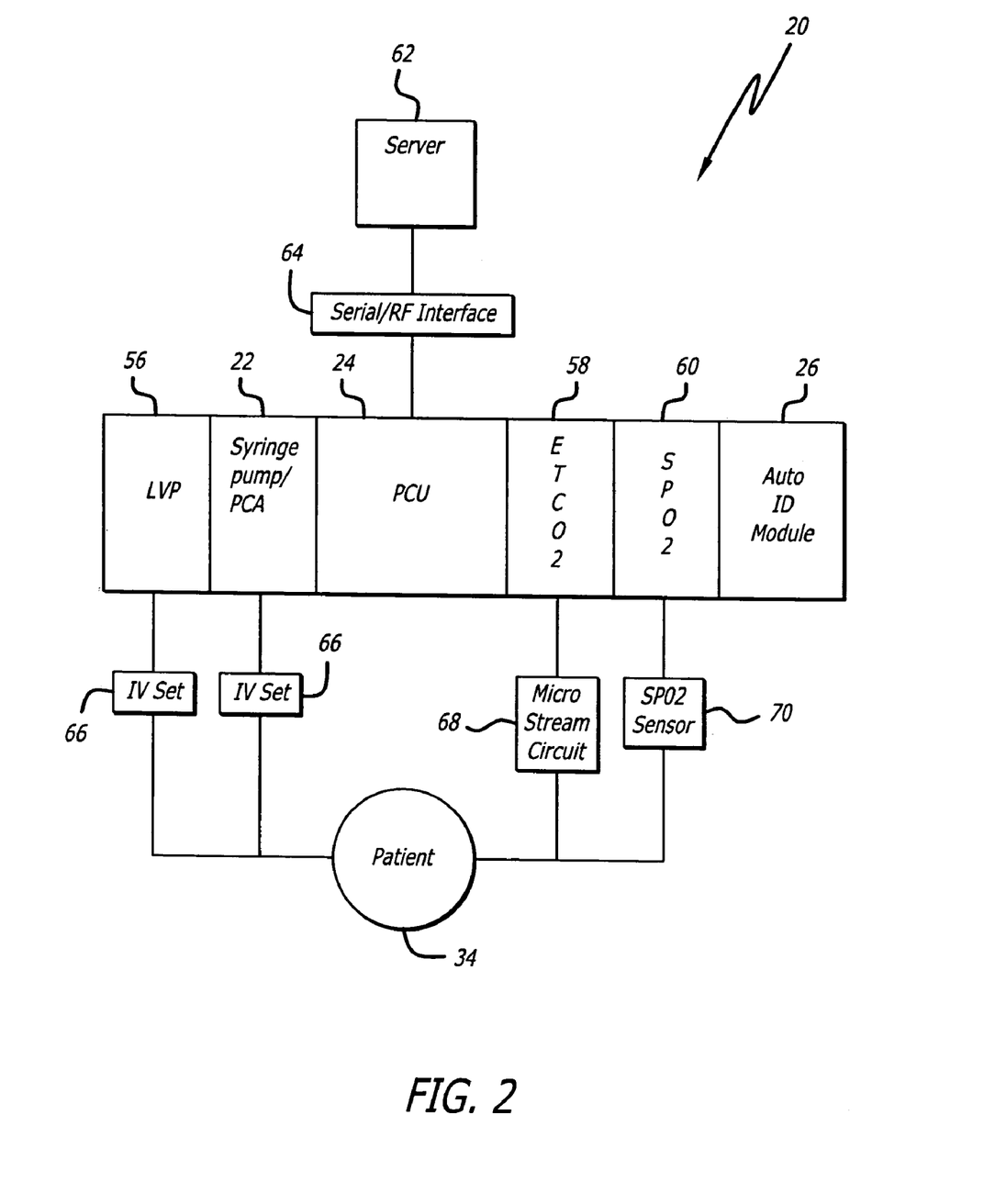
FIG. 2 is a block diagram of a modular infusion pump system also having a central controller, two infusion pumps (a large volume pump ("LVP") and a syringe/PCA (patient controlled analgesia) pump), and a pair of physiological monitors which in are an $ETCO_2$ module, and an $SPO_2$ module, and an ID module, all connected with the common controller connected to a remote server through a wired or wireless link.

Referring now to FIG. 2, there is shown a block diagram of a modular infusion pump system 20 having a central controller 24 (sometimes referred to as a "PCU"), two infusion pumps (an LVP 56 and a syringe/PCA pump 22), two physiological monitors comprising an $ETCO_2$ (end tidal carbon dioxide concentration in expired air) module 58, and an $SPO_2$ (blood oxygen saturation) module 60, all connected to a single patient 34 with the common controller connected to a remote server 62 through a wired or wireless link 64. Intravenous administration sets 66 communicate medications between the pumps and the patient, and the $ETCO_2$ sensor 68 and $SPO_2$ sensor 70 communicate physiological data to their respective modules. Further information concerning an $ETCO_2$ module is contained in U.S. Patent Application Publication No. 2003/0106553 to Vanderveen; further information concerning the $SPO_2$ module is contained in U.S. Pat. No. 5,957,885 to Bollish et al., both of which are incorporated herein by reference in their entireties. The ID module 26 is also connected to the set of IV and physiological sensing modules at the right side at the controller 24. This single ID module is applicable for all pump modules and physiological monitors controlled by the controller, as will be discussed below in more detail.

The controller 24 is shown connected to remote server 62 by wired connection or wireless connection. Various data may be communicated between the controller and server including, such as, for example, but not limited to, medication orders for the patient 34 communicated from the server to the controller, and status of medication administrations being administered to the patient communicated from the controller to the server. Other data may be communicated from the server to the controller such as drug library sets, drug profiles, and other data. It should also be noted that the infusion system 20 may take other forms, such as two syringe pumps and two LVPs, or four LVPs, or four syringe pumps, or any other combination, since the infusion system is modular in nature. The combinations presented in FIG. 2 are illustrative of an embodiment only and is not meant to be limiting of the invention.

Figure 3:
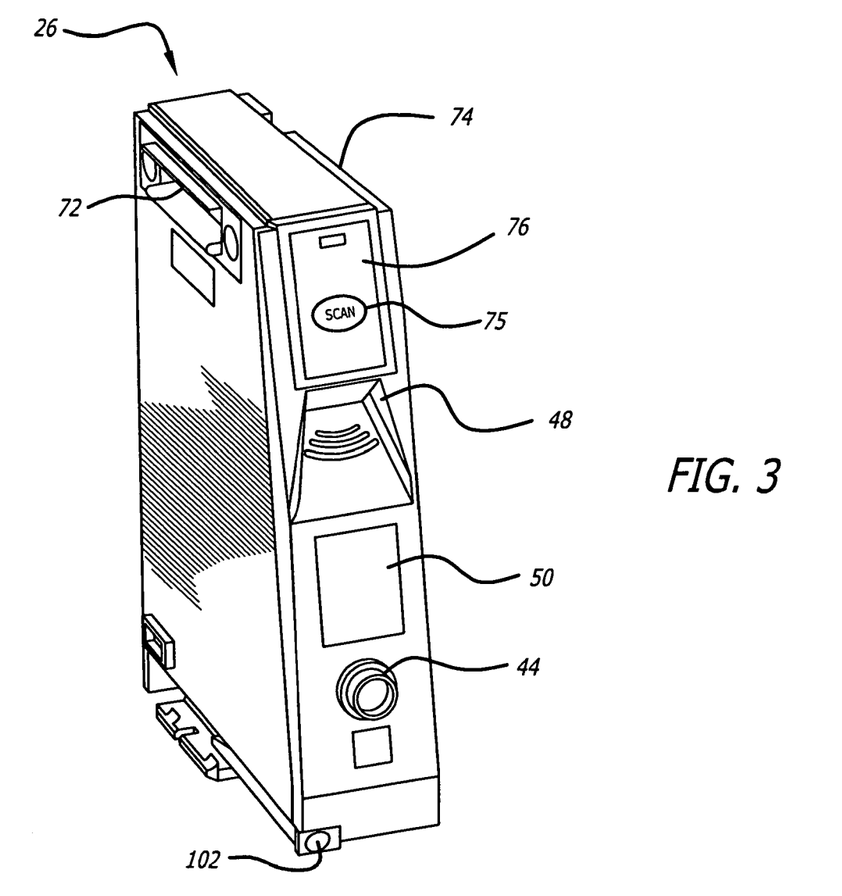
FIG. 3 is a perspective view of an embodiment of an ID module of FIGS. 1 and 2 showing a front panel fixed bar code reader, a connector to accept a complementary connector of a hand-held, mobile bar code reader, and the antenna of a fixedly mounted RFID interrogator or "reader"

Moving now to FIG. 3, a perspective view of the embodiment of the ID module 26 of FIGS. 1 and 2 showing a front panel fixed bar code reader 48, a connector 44 to accept a complementary connector of the hand-held, mobile, bar code reader 40 (FIG. 1), and the antenna 50 of the RFID reader, also fixedly mounted to the ID module. Further information concerning the means of connection of the ID module 26 to other modules through the IUI (Inter-Unit Interface) connectors 72 and 74 and channel release latch 102 are contained in U.S. Pat. No. 5,941,846 to Duffy et al., which is incorporated herein by reference in its entirety. The two IUI connectors permit its mounting at either its left side (as shown in FIGS. 1 and 2) or at its right side as desired.

The ID module 26 also includes a control panel 76. Although the control panel may take other forms, in this case, it includes a "SCAN" switch 75. This switch when pressed activates a reader so that an information device may be read. For example, pressing the SCAN switch 75 permits a clinician to place a bar code information device within the field of view of the fixedly mounted bar code reader 48 so that the information device may be read. Likewise, pressing the SCAN switch activates the hand-held, mobile bar code reader 40 and the RFID reader 50. In one embodiment, the SCAN switch is locked out when the pump 22 (FIG. 1) is infusing. In such a configuration, pressing the SCAN switch will not result in activation of any reader.

Figure 4:
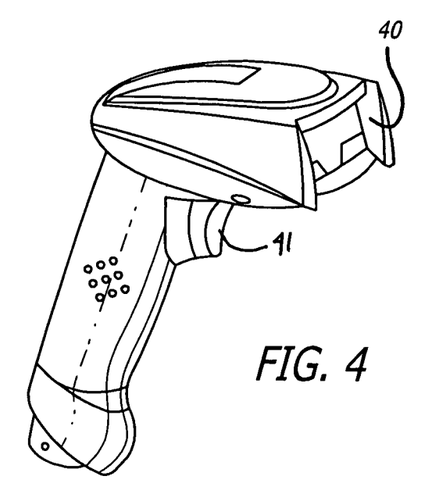
FIG. 4 is an example of a hand-held, mobile bar code reader or scanner usable with the cable that is connected to the front panel port of the ID module shown in FIG. 3 thereby "tethering" the hand-held scanner to the ID module.

Referring now to FIG. 4, an example of a hand-held bar code reader 40 or scanner is shown. This is a common type of bar code reader known to those skilled in the art and no further details of its structure or operation are provided here. Although not shown in FIG. 4, a cable 42 as shown in FIG. 1 may be used to connect the bar code reader to the ID module 26. Alternatively, the bar code reader may communicate wirelessly to the Auto ID. The hand-held scanner has a trigger 41 that will activate the scanner when pressed so that a bar code information device may be read. However, the front panel SCAN switch 75 must first be activated in this embodiment before the trigger will be activated.

As used herein, an "information device" is a device 11 at contains information readable by the particular technology for which it was designed. For example, a bar code is a barcode information device while a RFID tag is considered to be a RFID information device. Both contain information readable by their respective technology readers. Information devices and identification devices both include information.

Figure 5:
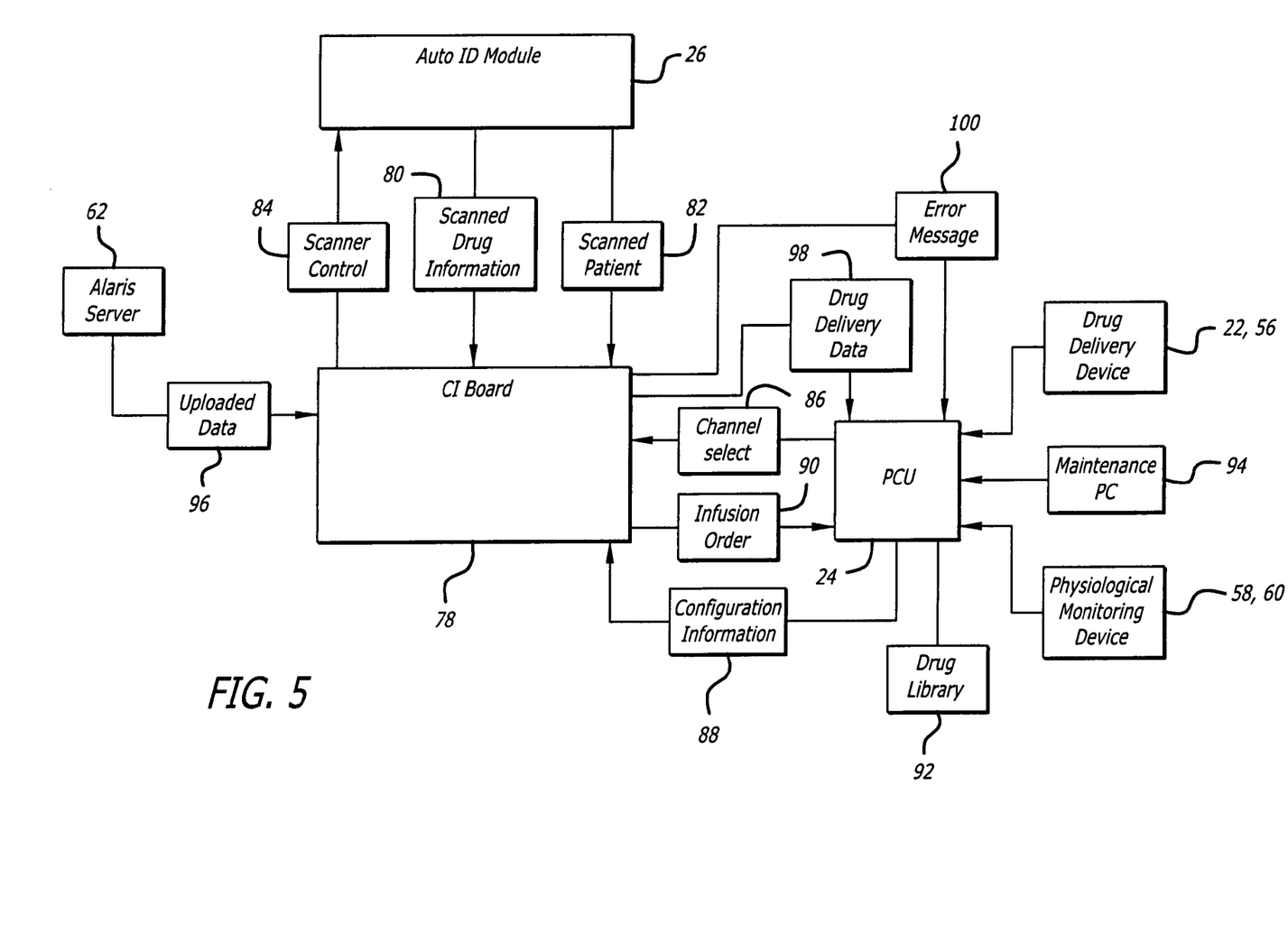
FIG. 5 is a block diagram of an embodiment of a system with the ID module of FIGS. 1 through 3 showing a central controller communicating with a drug library and a communications interface ("CI") board having a wireless communications interface processor with the CI board communicating with the ID module and a remote server.

Turning now to FIG. 5, a system is shown in which the ID module 26 directly communicates with a Communication Interface Board ("CI board") 78 over two spare communication lines. FIG. 5 shows the ID module communicating scanned medication information 80 and scanned patient identification 82. The medication information may include the medication name and concentration, and in another embodiment, may also include the rate of infusion and the dose for the medication. Although not shown, the ID module may also be used to scan a clinician's identification and to communicate that scanned clinician identification to the CI board.

The CI board 78 sends control signals 84 to the ID module 76. One example of a control signal would be a disable control signal to the ID module so that no bar code scanning can occur during the manual programming of an infusion pump. This would render the SCAN switch 75 ineffective. The controller 24 and CI board likewise communicate with each other. In the embodiment shown, for example, the controller sends a channel select signal 86 to identify which pumping channel 22 or 56 (FIG. 2) of the modular infusion system 20 (FIG. 2) the identified medication 80 is in.

Configuration data 88 is also sent from the controller to the CI board 78. Such data may comprise information concerning the configuration of data that will be transferred to the CI board, such as the format of data. Upon receiving an infusion order from a remote server 62 or other source, the CI board communicates the order 90 to the controller. The CI board operates as a communications interface processor.

The controller 24 also has access to a drug library 92. Further information on drug libraries is contained in U.S. Pat. No. 5,681,285 to Ford, which is incorporated herein by reference in its entirety. The drug library may be resident in the controller, in a local accessible memory, or may be located elsewhere on the system network but be accessible by the controller. "Drug Library Profiles" may be established in which medications, or drugs, and permitted concentrations, and permitted pumping parameters are set, such as, for example, an ICU (intensive care unit) profile, a pediatric profile, a neo-natal profile and others. Data sets of medications allowed for use and configurations of pumping parameters including limitations for that use may be available for each drug library profile. As such, drug library profiles may, although not necessarily, correspond to different patient care areas of the hospital. Thus a controller located in a pediatric ward, for example, will utilize a pediatric drug library profile that includes sets of allowed medications, pumping parameters, and pumping limitations that are specific to patients classified as pediatric or located in a pediatric ward. Similarly, a controller located in an ICU would utilize an ICU drug library profile that includes a different set of allowed medications, pumping parameters, and pumping limitations that are specific to patients located in an intensive care environment and other patients requiring intensive care.

A maintenance PC or server 94 is shown that performs updates, revisions, or other maintenance tasks for the controller 24. Finally, as alluded to above, the CI board 78 is connected to a remote server 62 having a management program that can upload data 96, such as medication orders and other data, to the CI board. It should be noted that although the CI board is shown as a separate element in FIG. 5, in another embodiment it may be integrated into the controller 24.

The scanned information 80 and 82 is sent directly from the ID module 26 to the CI board 78 for processing. The CI board then translates the scanned data and sends medication delivery data 98 or error messages 100 to the controller 24. The advantage here is that the burden of processing is placed on the CI Board and the ID module without burdening the controller 24 with additional computer processing of scanned data. This is advantageous in that such an arrangement avoids interrupting communications between the infusion or sensor modules and the controller.

Figure 6:
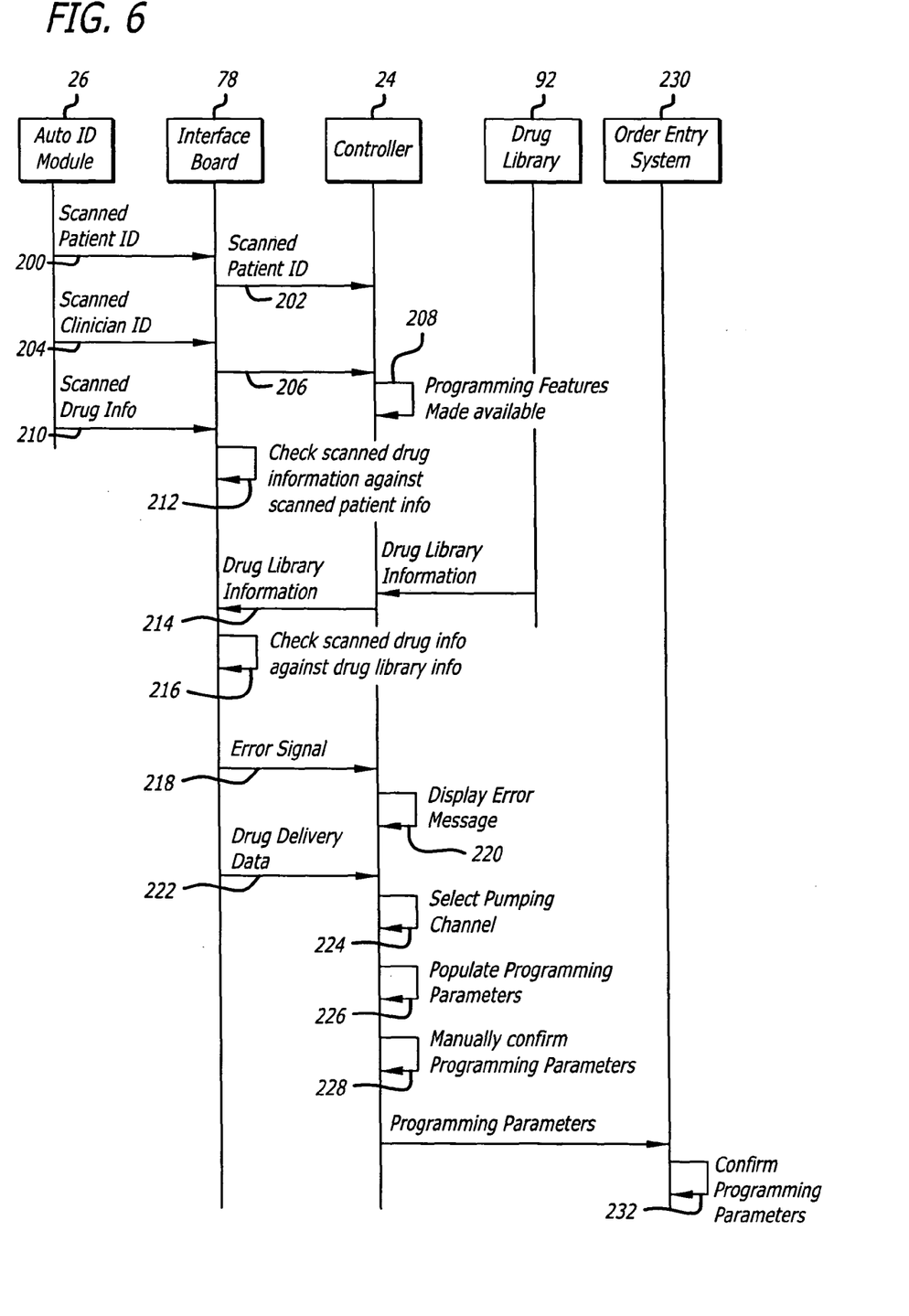
FIG. 6 is a flow chart of an exemplary identification system and method workflow in accordance with aspects of the invention showing confirmation of infusion parameters after automatic performance of checks of scanned medication information from the bar code on the syringe against scanned patient identification from the patient's wrist and information obtained from the drug library of FIG. 5.

In one embodiment, workflow of the system and method described above is illustrated in an exemplary process shown in FIG. 6. In the following description, the term "scan" or "scanning" or "read" or "reading" can refer to either bar code scanning or RFID scanning, or other data gathering techniques or technologies.

Upon initial power up of the infusion system 20 (FIG. 2), the infusion system prompts the clinician to associate the controller 24 with a patient 34. The patient may have a patient number or other scheme for identification. Similarly, drugs may have drug aliases or numbers for identification purposes. Using the embedded scanner 48, tethered scanner 40, or the RFID unit 50, the clinician scans the patient ID 82. This patient ID may have various patient information including a patient identifier, patient EMAR (electronic medication administration record), allergies, or other information. At step 200, the scanned patient ID is sent from the ID module 26 to the CI board 78 which then sends a message at step 202 to the controller telling it that it is now associated with the scanned patient ID. To administer a medication, the clinician scans his or her identification by the method described above. After the CI board receives the scanned clinician ID at step 204 and recognizes the clinician as having the appropriate authorization to administer the medication, the CI board signals the controller at step 206 to make available the medication programming features of the infusion system at step 208. In other embodiments, reading a clinician information device may not be required. The clinician, for example, then scans a medication container label 28 to obtain scanned medication information 80 for the label that contains, for example, a patient ID, a medication name, a medication concentration, and a medication dose. This information is then passed to the CI board at step 210 where the CI board:

1) checks to see if the scanned medication information contains the same patient ID that is associated with the controller to ensure the "right patient" at step 212,
2) automatically selects the drug library 92 entry for the scanned medication name at step 214 and check that the scanned medication name and medication concentration agrees with the drug library at step 216, thereby ensuring that the "right medication" and concentration are administered, and
3) automatically populates medication dose parameters at step 226 to, for example, the operating memory of the infusion module, thereby ensuring that the "right dose" of infusion medication is administered.

Prior to automatically populating medication dose parameters to the infusion module, alert messages may be displayed to the clinician at step 220 if the patient IDs associated with the controller and medication label do not match at step 212 or if the scanned medication name is not in the drug library profile that the controller is associated with at step 216.

Alert messages may also be displayed on the controller 24 when, for example, the scanned medication information 80 from a label 28 on a syringe 30 indicates that the syringe is to be administered to a patient named "John Smith" having a particular ID number, but the scanned patient ID 82 from a bracelet 32 worn by another patient 34 also named "John Smith" gives a different ID number or code. As a further example, an alert message may be displayed when the scanned medication information from a label on a syringe indicates that the syringe contains a medication having a particular concentration appropriate for an adult patient, but the controller is located in or is otherwise associated with a pediatric ward and the scanned medication name and/or scanned medication concentration does not match any entries in the pediatric profile in the drug library 92 accessed by the controller.

If all the scanned parameters are valid, the CI board 78 sends scanned medication delivery data 98 to the controller 24 at step 222. At step 224, the clinician selects the channel that the scanned medication will be administered on, and the drug library 92 entry as well as the programming parameters are automatically populated for the appropriate infusion pump or channel at step 226. The clinician must manually confirm that these parameters are correct at step 228. In a networked environment, these parameters could be checked with an order entry system 230, perhaps at the pharmacy, to verify at step 232 that the right order is being administered to the right patient.

It will be noted that a single bar code scanner or RFID scanner is used for all functional units controlled by the controller, regardless of the nature of the unit. The data derived by the scanner goes directly to the controller from the ID module, which then processes it before it reaches a pump unit or other unit. Whether it is a syringe pump 22, an LVP 56, or a physiological sensor, a single bar code reader or other scanner is used to provide identification information of the patient and other information as needed. The single scanner is therefore functional for multiple different medical units or instruments. Additionally, the bar code scanner is in a separate housing that is modular and detachable from the controller, as provided by release latch 102 (FIG. 3) and is not mounted in the housing of any medical instrument providing therapeutic treatment to a patient or in the housing of any instrument measuring physiological parameters of a patient. The scanner or ID module is therefore patient specific, rather than pump or "instrument" specific. For those healthcare facilities that desire bar code or RFID scanning, the ID module is easily mounted to the infusion system 20 and for those healthcare facilities that are not interested in such scanning, the ID module need not be a part of their inventory, yet the infusion system 20 will still function.

For those healthcare facilities that desire bar code scanning, one embodiment of the ID module 26 of the present invention may have two bar code scanners. One scanner is built into the front panel 48, while the other scanner 40 may be connected to the ID module 26 using connector 44 as desired. This redundancy provides an extra measure of utility to the ID module. Not only is the redundancy useful if one or the other scanner needs service, but if a patient's identification tag or device 32 cannot be placed near the built-in bar code scanner, a tethered or untethered scanner may be used to go to the patient's side and scan the patient's identification tag or device.

Referring once again to FIG. 6, the CI Board 78 may obtain limits for administering medication from the drug library 92 at step 214. Thereafter, at step 216, the CI board checks that the scanned medication information 80 agrees with the limits obtained from the drug library. If the two sets of information do not agree, an alert message is generated and sent by the CI Board at step 218 to be displayed by the controller 24 at step 220. For example, an alert message is displayed if the medication dose parameter obtained from the scanned label 28 on a syringe 30 intended to be administered to a pediatric patient exceeds medication administration limits that are predefined in a pediatric profile in the drug library accessed by the controller. Thus, administration errors are averted in cases where the scanned label, whether a bar code, RFID tag, or other machine-readable device, may have been improperly printed or programmed, may have been smudged or corrupted so as to give inaccurate data, or may simply be incorrect.

Additionally, drug library profiles may contain limits on infusions that are dependent upon a physiological level of the patient. In the case where a physiological monitor or monitors are is used, such as those shown in FIG. 2 where $ETCO_2$ 58 and $SPO_2$ 60 monitors are shown, the patient's particular monitored physiological levels would be compared against limits in the drug library profile and the infusion may be controlled as a result. Such physiological level limits in a profile may be drug specific or patient specific. For example, the drug library profile may have a patient physiological level limit for a particular drug regardless of the particular patient. In another case, patient-specific characteristics, such as recent medical history or allergies as examples only, may be considered when considering the impact that a measured physiological level of that particular patient should have on infusion of a particular drug. In another embodiment, both drug-specific and patient-specific considerations may be taken into account when monitoring patient physiological levels.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

We claim:

1. An identification system for medication management, the system comprising:
    a drug library comprising a plurality of drug library profiles, each one of the drug library profiles defining a list of drug identifiers associated with drugs allowed for use according to a patient care area of a hospital, and at least one of permitted concentrations and doses associated with each allowed drug;
    an identification module configured to scan drug information from machine-readable information devices affixed to drugs or containers of drugs and to scan patient information from machine-readable information devices worn by patients, and configured to communicate the drug information and patient information; and
    a controller in communication with the identification module, the controller configured to:
        receive information for a selected patient care area of the hospital;
        access the drug library associated with the selected patient care area of the hospital to associate a drug library profile with the controller;
        receive the patient information from the identification module;
        receive the drug information from the identification module, the drug information including a patient identification (ID) that indicates the patient for whom the drug is to be administered, a drug identifier and at least one of drug concentration and dose;
        determine whether the patient information received from the identification module from the machine-readable information device worn by a patient matches the patient ID contained in the drug information received from the identification module;
        determine whether the drug identifier and drug concentration or dose contained in the drug information received from the identification module match any entries in the list of drug identifiers, permitted concentrations, and permitted doses of the drug library profile for the selected patient care area that has been associated with the controller; and
        display an alert message if the scanned drug identifier and/or concentration does not match any entries in the drug library profile for the selected patient care area.

2. The system of claim 1 wherein the controller is configured to display an alert message when the patient information received from the identification module does not match the patient ID received from the drug or drug container.

3. The system of claim 1 wherein the controller is configured to display an alert message when the drug information received from the identification module includes a drug identifier that is not in the drug library profile associated with the controller.

4. The system of claim 1 wherein the controller is configured to display an alert message when the drug information received from the identification module includes a drug concentration that does not match the drug concentration information in the drug library profile associated with the controller.

5. The system of claim 1 wherein the controller is configured to display an alert message when the drug information received from the identification module includes a drug dose that does not match the drug dose information in the drug library profile associated with the controller.

6. The system of claim 1 further comprising a server in communication with the controller, the server configured to provide the controller with a medication order for the selected patient.

7. The system of claim 1 wherein the drug library is integral with the controller.

8. The system of claim 1 wherein the drug library is accessible by the controller through a remote server.

9. The system of claim 1 wherein the identification module is selectively detachable from the controller.

10. The system of claim 1 wherein the identification module comprises a bar code reader for reading bar code-type information devices.

11. The system of claim 1 wherein the identification module comprises a RFID reader for reading RFID-type information devices.

12. The system of claim 1 wherein the identification module comprises a hand-held mobile reader configured to read information devices located remotely from the identification module.

13. The system of claim 12 wherein the identification module further comprises a bar code reader fixed in position at the identification module for reading bar code-type information devices brought to its proximity to be read, and a RFID reader fixed in position at the identification module for reading RFID-type information devices brought to its proximity to be read.

14. The system of claim 13 wherein the hand-held mobile reader is connected with the identification module through a wired or wireless connection.

15. The system of claim 1 further comprising:
an infusion pump connected with the controller;
wherein the controller is adapted to provide programming parameters to the infusion pump that are received from the drug or drug container information device through the identification module.

16. An identification system for medication management, for use with an infusion pump, the system comprising:
an infusion pump;
a drug library comprising a plurality of drug library profiles, each one of the drug library profiles defining a set of drug identifiers that are associated with medications that are allowed for use according to a patient care area of a hospital, and at least one of permitted drug concentrations and drug doses associated with each allowed medication;
a controller configured to provide pumping parameters to the infusion pump and configured to receive information for a selected patient care area of the hospital; and access the drug library associated with the selected patient care area of the hospital to associate the controller with a drug library profile;
an identification module configured to scan drug information from machine-readable identification devices affixed to drugs or containers of drugs and to scan patient identification information from machine-readable identification devices worn by patients, and configured to communicate the drug information and patient identification information; and
a communications interface processor in communication with the controller and the identification module, the interface processor configured to:
receive patient identification information from the identification module;
receive drug information from the identification module, the drug information including a patient ID, a drug identifier, a drug concentration, and a drug dose;
determine whether the patient identification information received from the identification module matches the patient ID received from the drug information from the identification module, and determine whether the drug information received from the identification module matches the drug library profile for the selected patient care area based at least on comparisons between the received patient identification information, the received drug information, and the set of drug identifiers and permitted drug concentrations and doses from the drug library profile associated with the controller; and
provide, if all of the comparisons match, the controller with infusion pump programming parameters.

17. The system of claim 16 wherein the identification module is selectively detachable from the controller.

18. The system of claim 16 wherein the identification module comprises a bar code reader for reading bar code-type information and identification devices.

19. The system of claim 16 wherein the identification module comprises a RFID reader for reading RFID-type information and identification devices.

20. The system of claim 16 wherein the identification module comprises a hand-held mobile reader configured to read information devices located remotely from the identification module.

21. The system of claim 20 wherein the identification module further comprises a bar code reader fixed in position at the identification module for reading bar code-type information and identification devices brought to its proximity to be read, and a RFID reader fixed in position at the identification module for reading RFID-type information and identification devices brought to its proximity to be read.

22. The system of claim 16 wherein the infusion pump is selectively detachable from the controller.

23. An identification method for medication management, the method comprising:
associating with a computer processor a drug library profile with an infusion pump, the drug library profile including drug identifiers that are associated with medications that are allowed for use according to a patient care area of a hospital, and at least one of permitted drug concentrations and drug doses associated with each allowed medication;
reading with an identification module a machine-readable identification device worn by a patient to obtain patient identification information;
reading with an identification module a machine-readable identification device affixed to a selected drug or drug container to obtain drug information that includes a patient ID, a drug identifier, a drug concentration, and a drug dose;
receiving information for a selected patient care area of the hospital;
comparing with a computer processor the patient identification information from the identification device worn by the patient to the patient ID from the identification device affixed to the drug or drug container;
communicating by a computer processor a first error message when the patient identification information does not match the patient ID;
comparing with a computer processor the drug identifier from the identification device affixed to the drug or drug container to the set of drug identifiers of the drug library profile for the selected patient care area;
communicating by a computer processor a second error message when the drug identifier from the identification device is not within the set of drug identifiers of the drug library profile;
comparing with a computer processor the drug concentration from the identification device affixed to the drug or drug container to a set of permitted drug concentrations of the drug library profile for the selected patient care area;

communicating by a computer processor a third error message when the drug concentration from the identification device is not within the set of permitted drug concentrations of the drug library profile;
comparing with a computer processor the drug dose from the identification device affixed to the drug or drug container to a set of permitted drug doses of the drug library profile for the selected patient care area;
communicating by a computer processor a fourth error message when the drug dose from the identification device is not within the set of permitted drug doses of the drug library profile; and
providing with a computer processor, if all of comparisons match, infusion pump programming parameters, the programming parameters corresponding to the read drug dose.

24. The method of claim 23 further comprising manually confirming that the infusion pump programming parameters agree with a medication order for the patient.

25. The method of claim 23 wherein either step of reading further comprises reading with a reader that is fixed in position such that information or identification devices to be read must be moved to the proximity of the bar code reader.

26. The method of claim 23 wherein either step of reading further comprises reading with a reader that is mobile and hand-held such that the hand-held reader may be brought to the proximity of information or identification devices to be read.

27. The method of claim 23 wherein either step of reading further comprises reading with a reader that is optical.

28. The method of claim 23 wherein either step of reading further comprises reading with a reader that is non-optical.

29. An identification system for medication management, for use with an infusion pump and a physiological monitor, the system comprising:
a drug library accessible by the controller and comprising a plurality of drug library profiles, each one of the drug library profiles defining a set of drug identifiers that are associated with medications that are allowed for use according to a patient care area of a hospital, and at least one of permitted drug concentrations and drug doses, and physiological level limits;
a physiological monitor configured to measure a physiological level and provide a physiological signal;
an identification module configured to scan drug information from machine-readable identification devices affixed to drugs or containers of drugs and to scan patient identification information from machine-readable identification devices worn by patients, and configured to communicate the drug information and patient identification information; and
an infusion pump having a controller, a display, and an interface communications processor, the controller in communication with the display and physiological monitor, the interface communications processor in communication with the identification module, the controller, and drug library, the interface communications processor configured to:
receive information for a selected patient care area of the hospital;
associate a drug library profile for the selected patient care area with the controller;
receive patient identification information from the identification module from the machine-readable identification device worn by a patient;
receive drug information from the identification module from the machine-readable identification device affixed to a drug or drug container, the drug information including a patient ID, a drug identifier, a drug concentration, and a drug dose;
communicate a first error signal to the controller when the drug information includes a patient ID that does not match the patient identification derived from the machine-readable identification device worn by the selected patient;
compare the drug identifier from the identification module to the set of drug identifiers of the drug library profile for the selected patient care area and communicate a second error signal to the controller when the drug identifier from the identification module is not in the set of drug identifiers of the drug library profile associated with the controller;
compare the drug concentration from the identification module to the permitted drug concentrations of the drug library profile for the selected patient care area and communicate a third error signal to the controller when the drug concentration from the identification module is not in the set of permitted drug concentrations of the drug library profile associated with the controller;
compare the drug dose from the identification module to the permitted drug doses of the drug library profile for the selected patient care area and communicate a fourth error signal to the controller when the drug information includes a drug dose from the identification module is not in the set of permitted drug doses of the drug library profile associated with the controller; and
provide, if all of comparisons match, the controller with infusion pump programming parameters; and
wherein the processor is configured to display all error signals received from the interface communications processor, and to receive a physiological signal from the physiological monitor and display a fifth error signal when the physiological level from the physiological monitor is not within the physiological level limits in the drug library profile associated with the controller.

30. The system of claim 29 wherein the physiological level in the drug library profile associated with the controller is patient specific.

31. The system of claim 29 wherein the physiological level in the drug library profile associated with the controller is drug specific.

32. The system of claim 29 wherein the pump is selectively detachable from a central controller.

33. The system of claim 29 wherein the physiological monitor is selectively detachable from the controller.

34. The system of claim 29 wherein the identification module is selectively detachable from the controller.

35. The system of claim 29 wherein the infusion pump programming parameters correspond to the selected drug dose.

36. An automatic identification system for medication management, the system comprising:
an infusion pump;
a drug library comprising a plurality of drug library profiles, each one of the drug library profiles defining a set of drug identifiers that are associated with medications that are allowed for use according to a patient care area of a hospital, and at least one of permitted drug concentrations and drug doses associated with each allowed medication;
an identification module configured to scan drug information from machine-readable identification devices affixed to drugs or containers of drugs and to scan patient identification information from machine-readable identification devices worn by patients, and configured to communicate the drug information and patient identification information; and a controller in communication with the infusion pump and the identification module, the controller configured to:
- receive information for a selected patient care area of the hospital;
- access the drug library to obtain a drug library profile associated with the selected patient care area of the hospital;
- associate the obtained drug library profile with the controller;
- receive patient identification information from the identification module from the machine-readable information device worn by a patient;
- receive drug information from the identification module, the drug information including a patient ID, a drug identifier, a drug concentration, and a drug dose;
- determine whether the contents of the drug or drug container match the drug library profile for the selected patient care area based at least on comparisons between the received patient identification information from the identification module from the machine-readable information device worn by a patient, received drug information including the patient ID, drug identifier, drug concentration, and drug dose, and the set of of drug identifiers, drug concentrations, and drug doses from the drug library profile for the selected patient care area associated with the controller; and
- provide, if all of comparisons match, infusion pump programming parameters.

\* \* \* \* \*